US00PP22783P2

(12) United States Plant Patent
Wachter, III

(10) Patent No.: US PP22,783 P2
(45) Date of Patent: Jun. 12, 2012

(54) ***VERONICA* PLANT NAMED 'WHITEWATER'**

(50) Latin Name: ***Veronica* hybrid**
Varietal Denomination: Whitewater

(75) Inventor: John F. Wachter, III, Woodstock, IL (US)

(73) Assignee: Chicagoland Grows, Glencoe, IL (US)

( * ) Notice: Subject to any disclaimer, the term of this patent is extended or adjusted under 35 U.S.C. 154(b) by 308 days.

(21) Appl. No.: 12/661,876

(22) Filed: Mar. 25, 2010

(51) Int. Cl.
*A01H 5/00* (2006.01)

(52) U.S. Cl. ..... Plt./263.1

(58) Field of Classification Search ..... Plt./263.1
See application file for complete search history.

(56) References Cited

U.S. PATENT DOCUMENTS

| | | | | |
|---|---|---|---|---|
| PP18,073 | P2 * | 9/2007 | Theobald | Plt./251 |
| PP18,912 | P2 * | 6/2008 | Verschoor | Plt./263.1 |
| 2002/0069442 | P1 * | 6/2002 | Philpott | Plt./263 |

* cited by examiner

*Primary Examiner* — Wendy C Haas
(74) *Attorney, Agent, or Firm* — Penny J. Aguirre

(57) ABSTRACT

A new cultivar of *Veronica* plant, 'Whitewater', that is characterized by its white flowers, its foliage that is dark green in color with a lustrous surface, and its low spreading habit.

2 Drawing Sheets

Botanical classification: *Veronica* hybrid.
Variety denomination: 'Whitewater'.

BACKGROUND OF THE INVENTION

The present invention relates to a new and distinct cultivar of *Veronica* plant of hybrid origin and will be referred to hereinafter by its cultivar name, 'Whitewater'. The new cultivar of *Veronica* is a hardy herbaceous perennial grown for landscape use.

'Whitewater' was discovered by the Inventor in May of 2008 as a naturally occurring branch mutation of *Veronica* 'Waterperry' (not patented) that was growing in a one-gallon container at his nursery in Ingleside, Ill.

Asexual reproduction of the new cultivar was first accomplished by stem cuttings by the Inventor in May of 2008 in Ingleside, Ill. The characteristics of the new cultivar have been found to be stable and to reproduce true to type in successive generations.

SUMMARY OF THE INVENTION

The following traits have been repeatedly observed and represent the characteristics of the new cultivar. These attributes in combination distinguish 'Whitewater' as a new and unique cultivar of *Veronica*.

1. 'Whitewater' exhibits flowers that are white in color.
2. 'Whitewater' exhibits foliage that is dark green in color with a lustrous surface.
3. 'Whitewater' exhibits a low spreading habit.

The parent plant, 'Waterperry', differs from 'Whitewater' is having flowers that are blue in color. 'Whitewater' can also be compared to the cultivar 'Georgia Blue' (not patented), which is similar in being a hybrid *Veronica* with a low growing spreading habit. 'Georgia Blue' differs from 'Whitewater' in having blue flowers and in being taller in plant height.

BRIEF DESCRIPTION OF THE DRAWINGS

The accompanying colored photographs illustrate the overall appearance and distinct characteristics of the new

*Veronica*. The photographs were taken of a plant approximately one year in age as grown outdoors in a SVD 450 container in Glencoe, Ill. and forced into bloom after overwintering.

Figure 1:
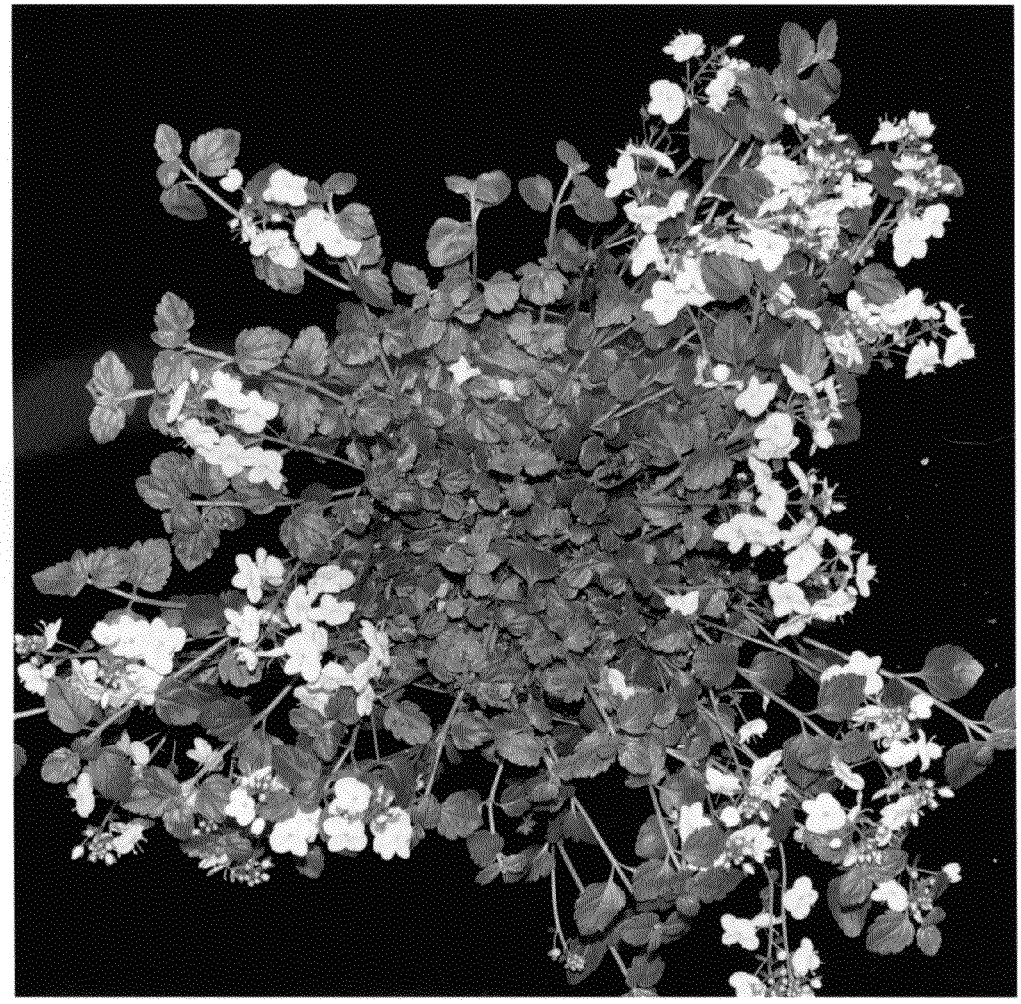

The photograph in FIG. 1 provides a top view of 'Whitewater' in bloom.

Figure 2:
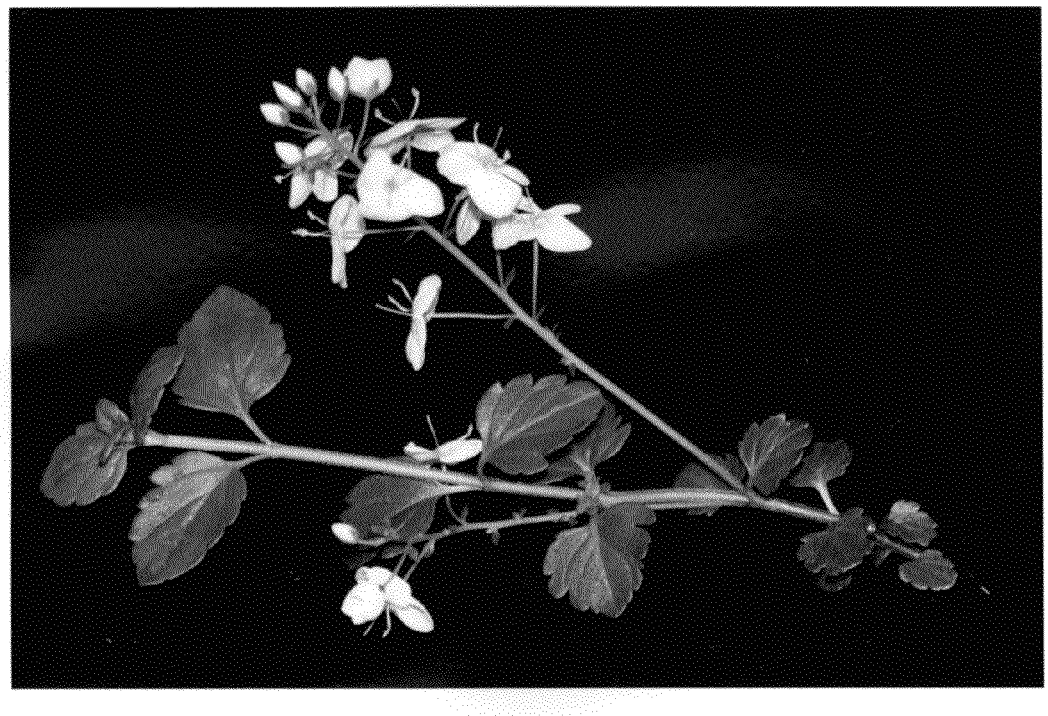

The photograph in FIG. 2 provides a close up view of a flowering stem of 'Whitewater'.

The colors in the photograph may differ slightly from the color values cited in the detailed botanical description, which accurately describe the colors of the new *Veronica*.

DETAILED BOTANICAL DESCRIPTION

The following is a detailed description of the new cultivar as observed for a plant grown in a 1-qt container in Glencoe, Ill. The phenotype of the new cultivar may vary with variations in environmental, climatic, and cultural conditions, as it has not been tested under all possible environmental conditions. The color determination is in accordance with the 2007 R.H.S. Colour Chart of The Royal Horticultural Society, London, England, except where general color terms of ordinary dictionary significance are used.

General description:

*Blooming period.*—4 weeks in mid spring.

*Plant habit.*—Herbaceous perennial, basal branching, prostrate plant habit, flowering stems emerging from axillary nodes.

*Height and spread.*—Reaches 10 to 15 cm (4 to 6 inches) in height with a spread of about 45 cm (18 inches).

*Hardiness.*—U.S.D.A. Zones 4 to 8.

*Diseases and pests.*—No susceptibility or resistance to diseases or pests has been observed.

*Root description.*—Fibrous.

*Propagation.*—Stem cuttings, root initiation occurs in 14 days at 85° F. under mist and a rooted cutting will develop in a 50-cell plug in 4 weeks at 85° F.

*Growth rate.*—Moderate.

Stem description:

*Shape.*—Oval.

*Stem color.*—Young; 147C, mature; 147B becoming heavily suffused with 177A.

*Stem size.*—Average of 1.3 mm in diameter and 21 cm in length.

*Stem surface.*—Pubescent.

*Branching habit.*—Emerge from base, an average of 12 branches as grown in a 1-qt container, occasional lateral branching.

Foliage description:

*Leaf division.*—Simple.

*Leaf arrangement.*—Opposite.

*Leaf shape.*—Ovate.

*Leaf size.*—An average of 1.6 cm in width and length when mature.

*Leaf number.*—Average of 18 per stem 18 cm in length.

*Leaf base.*—Broadly cuneate to truncate.

*Leaf apex.*—Broadly acute.

*Leaf margin.*—Crenate, about 4 per side.

*Leaf venation.*—Reticulate, recessed on upper surface and raised on lower surface, color matches leaf color becoming 144A near base on upper surface.

*Leaf surface.*—Puberulent on upper and lower surface, appearance is lustrous.

*Leaf aspect.*—Held primarily horizontal to stem on petioles held at about a 45° angle upward from stem.

*Leaf internode length.*—An average of 1.5 cm.

*Leaf color.*—Newly formed and mature upper surface; 137A, newly formed and mature lower surface; 137B.

*Petiole.*—Average of 5 mm in length and 1 mm in length, 144A in color, puberulent surface, sulcate in shape, held at about a 45° angle upward from stem.

Flower description:

*Inflorescence type.*—Racemes of rotate-shaped flowers from leaf axils.

*Lastingness of inflorescence.*—Individual flowers last 3 to 4 days, inflorescence lasts about 10 days, blooms from bottom of raceme towards apex.

*Inflorescence size.*—Racemes are about 6 cm in length and 1.8 cm in diameter.

*Flower type.*—Rotate.

*Flower number.*—About 12 flowers per raceme, an average of 2 racemes per stem.

*Flower fragrance.*—None.

*Flower buds.*—Elliptic in shape, about 4 mm in length and 2 mm in diameter, color 155A with calyx portion 137C.

*Flower size.*—About 2 mm in depth and 8 mm in diameter.

*Peduncles.*—About 5 cm in length and 1 mm in width, pubescent surface, 137C in color, flower internode length an average of 3.5 mm.

*Pedicels.*—An average of 7 mm in length and 0.7 mm in width, pubescent surface, 137C in color, one leaf at the base of each petiole; about 2.5 mm in length and 1.5 mm in width, oblanceolate in shape with all other characteristics similar to leaf.

*Calyx.*—Campanulate becoming spreading when flower is fully open, about 2 mm in depth and width and becoming 1.5 mm in depth and 4 mm in width when spreading.

*Sepals.*—4, un-fused, about 1 mm in width and 2 mm in length, 137B in color, surface is glabrous on upper and lower surface, elliptic in shape, acute apex, cuneate base, entire margin.

*Petals.*—4, orbicular in shape, rounded apex, fused at base to very short tube (<0.5 mm), entire margin, color of upper and lower surface 155A becoming very slightly flushed with 62D, up to 5 mm in length and width, glabrous and velvety surface.

Reproductive organs:

*Gynoecium.*—1 Pistil, style is about 4 mm in length, 0.4 mm in width and 155C in color, stigma is minute in size and 155C in color, ovary is superior, about 1 mm in diameter and 144A in color.

*Androecium.*—2 stamens, filament is about 4 in length, 0.4 mm in width and 155C in color, anthers are triangular in shape, about 0.7 mm in length, attachment is basifixed, and 155C in color, pollen is moderate in quantity and 161D in color.

*Fruit.*—Fruit and seed production was not observed under the conditions tested.

It is claimed:

1. A new and distinct variety of *Veronica* plant designated 'Whitewater' as described and illustrated herein.

* * * * *